United States Patent [19]
Lindsay et al.

[11] Patent Number: 5,504,014
[45] Date of Patent: Apr. 2, 1996

[54] DETERMINATION OF CONTAMINANTS

[75] Inventors: Alexander D. Lindsay, East Brunswick; Barry A. Omilinsky, Princeton Junction, both of N.J.

[73] Assignee: Formulogics, Inc., Trenton, N.J.

[21] Appl. No.: 90,632

[22] Filed: Jul. 12, 1993

Related U.S. Application Data

[63] Continuation of Ser. No. 655,506, Feb. 15, 1991.

[51] Int. Cl.$^6$ ............................ G01N 13/00; G01N 33/00
[52] U.S. Cl. ..................... 436/501; 435/7.72; 435/7.93; 436/56; 422/1; 422/90
[58] Field of Search ................ 436/501, 56; 435/7.72, 435/7.93; 422/1, 900

[56] References Cited

U.S. PATENT DOCUMENTS

| | | | |
|---|---|---|---|
| 4,233,192 | 11/1980 | Lindemann et al. | 252/545 |
| 4,421,858 | 12/1983 | Jackson | 436/20 |
| 4,659,676 | 4/1987 | Rhyne, Jr. | 436/56 |
| 4,755,469 | 7/1988 | Showalter et al. | 436/27 |
| 5,068,181 | 11/1991 | Driscoll | 435/13 |

FOREIGN PATENT DOCUMENTS 0327163  8/1989  European Pat. Off. ....... G01N 33/26

*Primary Examiner*—Michael P. Woodward
*Attorney, Agent, or Firm*—Larson and Taylor

[57] ABSTRACT

The cleanliness of water-rinsed surfaces originally carrying hazardous compositions is determined by using a surface active agent as a marker in said material prior to placing the composition into contact with the surface.

19 Claims, No Drawings

DETERMINATION OF CONTAMINANTS

This application is a continuation of Application Ser. No. 07/655,506 filed Feb. 15, 1991.

BACKGROUND OF THE INVENTION

This invention relates to a method of determining the amounts of contaminant remaining on surfaces of interest to an individual or an agency. More particularly, the invention relates to a method of determining when a container or any surface is sufficiently free of contaminants.

A problem associated with the use of pesticides and other materials treated as, or perceived to be hazardous, is the safe disposal of the container.

A number of the pesticides registered with the EPA instruct the user to dilute them with water prior to application to the selected target. By state and federal law, these containers must be triple-rinsed with a volume of water equal to 10–30% of the original volume, or pressure rinsed for at least 30 second before the container can be discarded. When either of these two actions have occurred, the container can be considered as non-hazardous waste. However, since it is very difficult to prove that the container has been rinsed and since extremely small amounts of residual products may cause future problems, most pesticide containers are not readily accepted in landfills. This reluctance on the part of landfills to take containers means that either state or federal programs must be established to collect, inspect and dispose of the containers. Even under these conditions it is difficult for the state or federal agents to insure that the containers are acceptable. The only way to determine that rinsing techniques have effectively cleaned the container and rendered it suitable for disposable is to analyze the water remaining in the rinsed container. For a vast majority of users such analyses are very expensive, time-consuming and impractical. This same problem of establishing that the container has been properly rinsed holds true for the homeowner who elects to safely dispose of pesticide, paint, bleach, pool chemicals or household cleaner containers.

Most programs for confirming the cleanliness of the container rely on visual inspection coupled with checking for the remnants of any solvent odors. With proper training this can be used successfully with odiferous products and those that are highly colored. Unfortunately, there are many hazardous products which are odorless and colorless.

Another method relies on analytical procedures for the detection of specific contaminants. This procedure becomes very prohibitive when several different chemicals are being used. Such analytical techniques include but are not limited to spectophotometric analysis, immunoassay techniques, gas and liquid chromatography, mass spectroscopy and nmr procedures. Thus, the difficulty being experienced by the federal, state and local officials and the consumer is the fact that there are a multitude of products requiring a proper rinse procedure and no single method of analysis available to detect container cleanliness. The various physical forms of these hazardous products such as wettable powders, flowables, emulsifiable concentrates and granulars also add to the analytical problem.

Recently, European Patent Application No. 0 327 163 suggested a means of marking products to prevent the dilution of, or the substitution of one product for another. It discloses the concept of tagging the product with a marker compound that could be analyzed for or identified by immunoassay. The patent application calls for the introduction of a marker compound to the desired product. One could later prove the validity of the sample by either analyzing the sample as is (water-based product) or first extracting the product to move the marker into a water phase and then analyzing by immunoassay.

Unfortunately, the detection method of the European Patent Application No. 0 327 163 does not provide a satisfactory solution to the problem of ascertaining whether a container is sufficiently clean so that it is ready for disposable. First of all, the method of the European Patent Application uses a marker concentration in the range of 25 ppm to 1 ppb. This concentration range represents the detection limits of the immunoassay procedure, i.e., the method has been designed to determine the concentration of the marker as originally added, not upon dilution. Thus, when a container of a product containing the marker at the prescribed level is rinsed according to the current procedures, the marker concentration in the final rinsate is reduced to much below the detectable concentration. Since a rinsed container is usually considered to be clean when 99.9999 of the original concentration of the hazardous product has been removed it is evident that the marker concentration in the rinsate would be well below any detectable level.

Secondly, the marker used in the European Patent Application is substantially water-soluble. Consequently, when the marker is used in an oil-based product it must be extracted, reduced in volume and dissolved in water or a water/methanol mixture so that the analysis can occur. This multi-step operation is tedious and cumbersome.

Thirdly, since the marker is water-soluble, unless it is used in a water-based product, it would not behave in a manner analogous to the bulk product that was being tagged. As the product was rinsed from the container the water soluble compound would dissolve in the rinse water at a rate disproportionate from the active ingredient. This would result in a false indication of a clean container.

Lastly, the marker compounds disclosed in the European Patent Application are identified as metabolities of the EPA registered insecticide cypermethrin or meta phenoxybenzoic acid and dichlorovinyl cyclopropane carboxylic acid. Since these compounds are recognized metabolites of the insecticide cypermethrin, the presence of these compounds in crops or crop related products is regulated by the FDA. Hence using this type of compound would be in essence using a pesticide to act as a marker for another compound. In an environmentally conscious society use of such compounds is not an acceptable approach to the problem.

It is therefore an object of the invention to provide a method of determining the amount, if any, of contaminants remaining on surfaces.

Another object of the invention is to provide a method for using a single analytical procedure to monitor the successful rinsing from a container of any contaminated product designed for use with water.

Another object of the invention is to provide a simple, economically attractive method enabling both the customer and state and federal officials to easily monitor the proper removal of the specified products from containers.

Yet another object of the invention is to provide a method for accurately determining the residual amount of contaminated product remaining on a rinsed surface such as that of a container or post-harvest produce, by using a marker which behaves in a manner analogous to the tagged bulk product.

An additional object of the invention is to provide a method of monitoring the movement and concentration of a product in the environment.

A further object is to provide an assay kit with which the customer or government official can rapidly determine whether a surface is contaminant-free without recourse to laboratory facilities.

SUMMARY OF THE INVENTION

These and other objects are provided by tagging a composition comprising a known concentration of a contaminant with a predetermined amount of a surface active agent as a tag or marker prior to placing the composition into contact with a surface. When the resulting surface is rinsed with water, a sample of a known volume of said aqueous rinsate is taken and the amount of surface active agent therein is determined. The determined amount of surface active agent relative to the predetermined concentration of said contaminant provides a measure of the amount of contaminant remaining on the surface.

Since the concentration of contaminant and the concentration of marker in the original product, and the volume of sample rinsate are all known quantities, determination of the concentration of surface active agent in the rinsate provides all the information necessary to calculate how much contaminant remains on the surface.

By the term "surface" as used herein and the appended claims is meant any surface on or with which contaminated compositions have come into contact and include, for example, the inner or outer surface of a vessel of any shape or size, the surface of filters or other devices designed to concentrate residues from a gaseous or fluid state of the surface of animal, plant or synthetic surfaces.

Any suitable detection system can be utilized to determine the absence or presence of the marker compound and/or its concentration. In its most convenient application, the User simply places a small quantity of rinse water from the empty container into contact with a colormetric indicator medium or analyzes it per the instructions on a test kit and awaits a reaction. A reaction, in turn, signals the presence or absence of the marker. Since the system can be titrated by conventional methods to provide a reaction at a given concentration of the marker compound, the detection mechanism can be used to show that the surface has been properly rinsed.

Also, the initial concentration of the marker compound contained in any specific product can be adjusted to any pre-set percentage established by an appropriate regulatory agency. It is therefore feasible to calculate the final concentration of the marker compound remaining in a container after a rinsing procedure. As a result, the failure of a prescribed rinsing procedure to detect the marker compound means that the container is sufficiently cleaned and ready for disposal, consumption or use.

The contaminated compositions with which the invention is concerned are compositions comprised of a contaminant, usually as an active ingredient in a carrier media which forms an immisible phase with water. Illustrative of such compositions are oil or solvent-based products and water-based suspensions, wettable powders, water dispersible granulars, tablets or dust. Thus, when, for example, an emptied container is rinsed with water, the rinsate system exists as a water/oil (or solvent) or a water/solid interface. As a result, these systems present a risk of disproportionate marker loss since marker compounds heretofore employed are preferentially soluble in one or the other of the phases. The preferential entry of the marker into one of the phases could give a false indication of the level of contaminant remaining in the container. Use of surface active agents as the marker compound avoids this risk since the surface active agent associates itself with the item desired to be removed by positioning itself between the two phases and behaving as part of the entire oil or solid/surfactant/water system.

In markets such as the pesticide industry, the products that would be tagged are usually sold in containers that are in turn emptied into other vessels so that they can be applied to the target. These original containers and those used to apply the product must be rinsed with water after use. With each rinse the level of the original product, including the contaminant, in the container is decreased due to the product partitioning into the rinse water. The surface active agent marker being associated with the contaminant and positioned at the interface will behave in a manner analogous to the contaminant and its level in the water rinse will be directly proportional to that present in the original product.

In another aspect, the invention provides an article of manufacture for use in an immunoassay kit comprising a testing vessel such as a test tube internally coated with an antibody specific to a surface active agent.

In yet another aspect of the invention, an assay kit for detecting surface active agent marker in rinse water is provided which comprises immunoassay means comprising antibodies specific to a surface active agent and means for detecting the results of the immunoassay.

DETAILED DESCRIPTION OF THE INVENTION

The Marker

The marker compound of the invention is selected from a class of chemicals referred to as surface active agents. Any of the surface active agents commonly added to preparations destined to be diluted with water are contemplated and include surfactants of the anionic, cationic, Zwitterionics and non-ionic type. In the method of the invention, the surface active agents work by associating themselves with the non-aqueous phase and on the addition water by uniting or positioning themselves at the interface of the immisible phases. Thus, as the product is rinsed with water from the container the surface active agent moves with the non-aqueous phase be it an oil phase or a solids phase as in the case of flowables, wettable powders, water dispersible granulars, tablets or dust.

Illustrative of surface active agents suitable for use as markers in the present invention are the following:

A. Anionics

1) Carboxylic acid salts, e.g. sodium and potassium salts of straight chain fatty acids of 10–20 carbon atoms, preferably sodium and potassium salts of fatty acids, tall oil acids; amine salts, e.g. triethanolamine; N-lauryl sarcoside;

2) Sulfonic acid salts, e.g. linear sodium or calcium alkyl benzenesulfonates, benzene-, toluene- and cumene sulfonates, lignin sulfonates, petroleum sulfonates, paraffin sulfonates, -olefin sulfonates, sulfosuccinate esters and alkylnaphthalene sulfonates;

3) Sulfuric acid ester salts, e.g. sulfated linear primary alcohols of 16–20 carbon atoms; sulfated polyoxyethylenate straight chain alcohols and sulfated triglyceride oils; and 4) Phosphoric and polyphosphoric acid esters, e.g. phosphated polyoxyethylenenated long chain alcohols and phenols.

B. Cationics
1) Long-chain amines and their salts, e.g. primary amines derived from animal and vegetable fatty acids, tall oil, and synthetic $C_{12}$–$C_{18}$ primary, secondary or tertiary amines;
2) Diamines and polyamines and their salts, e.g. N-alkyltrimethylenediamine and N-alkylimidazoline salts;
3) Quaternary ammonium salts, e.g. N-alkyltrimethylammonium chloride and N,N-dialkyldimethylammonium chloride;
4) Polyoxyethylenated long-chain amines, e.g.

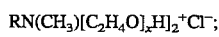
$RN(CH_3)[C_2H_4O]_xH]_2^+Cl^-$;

5) Quaternized polyoxyethylated long-chain amines, e.g.

$RN(CH_3)[(C_2H_4O]_2^+Cl^-$;

6) pH-sensitive Zwitterionics, e.g. β-N-alkylaminopropionic acids, N-alkyl-β-iminodipropionic acids and imidazoline carboxylates.

C. Non-Ionics
1) Polyoxyethylenated alkylphenols, e.g. polyoxyethylenated p-nonylphenol, p-octylphenol or p-dodecylphenol, derived from diisobutylene, propylene trimer or propylene tetramer;
2) Polyoxyethylenated straight chain alcohols, e.g. derived from coconut oil, tall oil or synthetic straight chain alcohols;
3) Polyoxyethylenated polyoxypropylene glycols, e.g. having a molecular weight of 1000–30000;
4) Polyoxyethylated mercaptans;
5) Long-chain carboxylic acid esters, e.g. glyceryl and polyglyceryl esters of natural fatty acids, sorbitol and polyoxyethylenated sorbitol esters, and polyoxyethylene glycol esters and polyoxyethylenated fatty acids; and
6) Alkanolamides, e.g. alkanolamine fatty acid condensates.

The amount of surface active agent marker added to the contaminant-containing product will range from about 1 to 10% by weight, depending principally upon the particular product being tagged and the level of detection desired. The marker can be added to the finished goods or it can be added by the manufacturer at the time of manufacture. In the former case, it would be necessary to recalculate the potency of the product. In the latter case, the manufacturer could withhold a portion of the surfactants usually employed equal in amount to that of the marker being added without adversely effecting the potency or performance of the final product.

Also, while the marker employed will usually be a surface active agent dissimilar to those normally employed in the product, the invention contemplates using the existing surface active agents as the marker, particularly in cases where the level of such surface active agents is below 10% by weight. Moreover, the EPA and FDA has approved surfactants for use in animal, food and crop protection chemical formulations and therefore its addition or substitution to these products poses no regulatory problems.

THE CONTAMINANTS

The method of the invention can be used to detect any contaminants which associate with the surface active agent either directly or indirectly through the non-aqueous media which carries the contaminants.

The term "contaminant" as used herein and the appended claims means any undesired substance but normally will be a hazardous toxic substance.

In most instances the invention will have its greatest application in the detection of products hazardous to health and/or the environment whether used at home, on the farm or in industry.

Pesticides chlorinated hydrocarbons, e.g. lindane, chlorothalonil, 2,4-D salts and esters, permethrin, bifenox, acifluorfen, organophophates, e.g. fonophos, ethoprop, malathion, parathion, disulfoton, acephate, dimethoate, carbamates, e.g. carbofuran, carbaryl, zineb, molinate, bendiocarb triazines, e.g. atrazine, propazine, hexazinone, secbumeton anilides, e.g. alachlor, fluchloralin, propanil, propachlor, benefin organometallics, e.g. phenylmercuric acetate, methanearsonic acid amines esters and salts, tributlytin salts and esters, copper oleate, zinc naphthanate general nitrogenous compounds, e.g. picloram, captan, aldicarb, etridiazole, bentazon, Diene based endrin, endosulfan, aldrin, methoprne Urea and uracils, e.g. monuron, linuron, tebuthiuron nitrated hydrocarbons, e.g. trifluralin, dinoseb miscellaneous category, e.g.

inorganic—zinc phosphide, mercurous chloride, organic—warfarin, alar, piperonyl butoxide, propargite, m-rotenone

Household Toxic Materials

Latex paints, lye, turpentine, bleach, glass cleaners, antifreeze, animal sprays and the like.

WATER-IMMISIBLE MEDIA

The contaminants determined by the method of the invention may be carried in a media which forms an immisible phase with water. Such media include organic or solvent-based systems which form, on mixing with water, an oil/water interface. They may also be delivered as dispersible powders or particulate or encapsulated suspensions.

Examples of organic substances which form an oil/water interface are aromatic solvents such as benzene, toluene, ethylbenzene, xylene, cumene, alkyl-substituted benzenes, aromatic alcohols such as phenol, and the like;

aliphatic solvents such as n-pentane, n-hexane, n-3-methylhexane, n-octane, n-decane, cyclo pentane, cyclohexane, and the like;

oils derived from patent sources such as soybean oil, cottonseed oil, corn oil, etc.;

fatty acid derivatives such as lauryl sulfates; and partially water-soluble chemicals such as N-methyl pyrrolidone, dimethylformamide, etc.

Examples of water-based suspensions are aqueous slurries of:

carbaryl (Sevin®), carbofuran (Furadan®) and chlorothalonil (Bravo®); and water-insoluble organic dyestuffs, tanning oils, cutting oils, medical ointments, household detergents, polishes, cosmetics, wood stains, paints, aerosols, fertilizers, etc.

Examples of encapsulated suspensions are
1) Penncap-M® (a polymeric microcapsule of methyl parathion in a water-based suspension); and
2) Lasso Micro-Tech® (a polymeric microcapsule of alachlor in a water-based suspension).

Examples of wettable powders are
1) Ortho Rotenone Dust or Spray® (a dry composition containing rotenone that can be added to a given amount of water to produce a suspension); and
2) Orthocide® (Captan) Garden Fungicide (a dry composition containing captan that can be added to a given amount of water to produce a suspension).

Examples of water dispersible granules are
1) AAtrex 90® (a dry composition of atrazine that has been granulated to reduce the dustiness of the original powder. The product is used by adding a given amount of the product to water, then agitated to form a suspension); and
2) Beacon® (a dry composition containing 75% w/w primisulfuron that has been granulated to reduce the dustiness of the original powder. The product is used by adding a given amount of the product to water, then agitated to form a suspension).

As aforementioned, both types of media often are designed to be mixed with water and sprayed onto a target area as, for instance, farm crops and, therefore, normally contain one or more surface active agents to insure application of the active ingredient in a uniform manner.

In the case of hazardous materials contained in oil- or solvent-based media, the consumer uses the product by diluting same with water prior to application on the desired target. As the product is added to the water phase an emulsion is formed. That is, small particles of the oil phase are generated in the continuous water phase and are stabilized due to the presence of selected emulsifiers at the surface of the oil droplets. The formation of the emulsion insures that the product will be applied in a uniform manner. In addition to the emulsifiers commonly present in the emulsion sprayed, the marker compound will also reside at the oil/water interface since it too, is a surface active material.

The material that remains in a container or on another surface is then rinsed out by adding additional amounts of clean rinse water. As the water is added to the product an emulsion is formed and this emulsion is added to the spray tank. This procedure is repeated two more times if the user is following typical triple rinse procedures. As long as there is sufficient product to generate an emulsion the surfactants and marker will remain in contact with the oil phase. Thus, the detection of the marker compound can be used to infer that the active material is still present in the rinse water. Once the product in the container has been rinsed sufficiently there will either be no product left to form an emulsion, or the remaining product has been diluted to the point where it is soluble in the water phase, hence existing as a solution rather than an emulsion. In either case the dilution at this point should be sufficient to render the remaining amount of active ingredient as non-harmful. The level of marker left at this point will be below that of the detection capabilities of the test procedure. Hence the lack of a positive test for the marker compound can be used to show that the rinse procedures are sufficient to render the container safe to discard.

When dispersible powders, particulate or encapsulated suspensions are diluted in water the small particles of the active ingredient are suspended in the water phase. This is accomplished by the proper selection of surface active agents which orient themselves on the surface of the solids and confer stability to the particles due to steric and electronic repulsions. As this product is rinsed from the container the surface active agents move with the solids. Therefore, as the solids are depleted so are the surface active agents. To test for the cleanliness of the container one only has to test for the presence of the marker in the rinsate. Since the marker is a surface active agent it is intimately associated with the particles of the active material. Therefore, as the suspension is diluted there is a partitioning of the surface active agents between the water phase and the individual solids particle. This means that as long as there are solids to be removed from the container there will be a marker compound available to be analyzed in the water phase. A positive test for the surface active agent/marker thus indicates that there is still a significant amount of the active compound in the container and that further rinsing is required. A negative test for the marker means that sufficient dilution has occurred and that the container can now be discarded in a safe manner.

Any suitable method of determining the amount of surface active agent in the aqueous rinsate can be employed as, for example, gas-liquid chromatography with or without mass spectroscopy, high performance liquid chromatography, ultra-violet spectrophotometry, gel permeation chromatography and immunoassay techniques.

Preferred amongst the various analytical methods are the well known immunoassay techniques such as enzyme-linked immunosorbent assay (ELISA), enzyme-mediated immunoassay and sandwich immunometric assays. The immunoassay is carried out by using antibodies specific to the selected surface active agent. These may be either polyclonal antibodies or monoclonal antibodies and are prepared by known techniques. In general, the antibodies are raised by injecting an animal with the selected surface active agent per se, if it is immunogenic, or the surface active agent (hapten) chemically combined with an immunogenic carrier such as a protein (e.g. bovine serum albumin) if the surface active agent itself is not immunogenic. Injection of the animal with the immunogenic substance produces polyclonal antibodies. Should antibodies with greater specificity to the surface active agent be desired, monoclonal antibodies may be obtained by extracting β-cells from the spleen of the immunized animals and fusing them to myeloma cells to produce hybridomas. The hybridomas are then cloned and tested to determine which produce the desired antibody. Large quantities of the desired antibody can then be obtained for the selected monoclonal antibody.

In accordance with the invention, the surface active antibody thus obtained is placed in test vessels for use in test kits for determining the presence or absence of the surface active agent in the emptied containers. Most preferably, the test vessels are internally coated with the antibody using proprietary techniques which insure the chemical integrity and stability of the antibody. The test vessel can be glass or plastic test tubes or may be micro titer strips containing 12 treated wells per strip.

Assay kits for use in the method of the invention can comprise a test substrate having fixed thereto antibody specific to the surface active agent in combination with colorimetric detection means. The test substrate is usually a vessel such as a test tube or a well but can be any substrate onto which the antibody can be immobilized.

The most popular immunoassay colorimetric detection means comprises an enzyme-surface active agent conjugate chromogen and substrate. According to this detection method, when the contents of the marked container is used up and the container rinsed as by triple rinsing, an aqueous sample is taken from the container and added to the test substrate, e.g. a test tube, having the antibody specific to the marker immobilized on its internal surface. An enzyme/surface active agent conjugate is then added to the test tube and after a period of time, for example, 5 minutes, the contents of the test tube is poured out and rinsed with water. The substrate solution is then added; followed by chromogen solution. Within minutes, color development should be sufficient to indicate a "pass or fail" situation. The same procedure is followed with an unmarked sample as a negative control. The development of a color in the marked sample equal to that of the control indicates the absence of the marker. The lack of color indicates the presence of the marker and therefore the water sample still contains the products at levels above the established limits.

In addition to determining if containers of contaminated products have been properly cleansed, it is expected that the invention will find extensive use in determining whether post-harvest crops are free of hazardous chemicals before distribution to the public. Thus the invention can be used to determine how much is present after washing with water. The analyst simply collects the sprayed produce, washes it with water, collects a known volume of rinse water and tests it for the amount of marker present.

Again, as aforementioned, the test can be a simple go/no-go test with the limits of detection preset when the detection method is formulated. An example is a coupon which is moistened with a predetermined amount of the rinse water and allowed to incubate for a brief period of time resulting in a color change which gives a go/no-go indication. Alternatively, the analyst can use a series of calibrated standards and determine the amount of product present.

In addition, the method of the invention can be used to determine if standard processing procedures can effectively remove contaminated products from the crops. The analyst merely assays the various aqueous process and waste streams for the presence of the marker and, if desired, monitors its movement during processing.

Another application of the invention involves determining and/or monitoring the amount of contaminant that has been deposited on an intended target and how much has been deposited off-target. Illustrative of intended targets are edible farm crops, trees, shrubs and grasses, application equipment, rinse pads, water and animate and inanimate surfaces commonly treated with pesticides and other toxic materials.

Examples of off-targets are soil, water, the applicator and/or flagman, other crops not intended for application and the like. In these applications, the marker is introduced into the product either at the point of manufacture or at the application device. The concentration which is selected depends upon the level of detection desired and a marker having physical properties that match the target are chosen. Once the application is complete the targets and non-targets are gathered, water-washed and an aqueous rinsate sample analyzed to determine the presence and/or amount of marker.

Another use of the present invention could be to monitor the movement of a contaminant through a production facility such as a chemical plant. Collection means could be established in selected locations and as the contaminant moves through the manufacturing process or as the equipment is decontaminated, aqueous samples can be taken and tested for the present of the marker. This would allow the monitoring of leakage, spills and other forms of fugitive emissions, whose presence individuals would desire to eliminate.

The following examples are given to further illustrate the present invention.

EXAMPLE I

To a container containing a crop-protection chemical formulation is added 1% by weight octylphenoxypolyethylene oxide as a marker. The resulting composition comprises:

| Alachlor | 44.0% |
|---|---|
| Petroleum Distillate | 20.0% |
| Emulsifier system | 5.0% |
| Marker | 1.0% |
| Monochlorobenzene | 30.0% |
| | 100.0% |

The container is emptied and filled with 25% of its volume of clean water and shaken for at least 30 seconds. The rinsate is discarded and the procedure repeated three times. The fourth rinsate is taken and analyzed for the presence of the marker by the immunoassay described in Example II below.

EXAMPLE II

Preparation of Antibodies Specific To Surfactant and Immunoassay Kit

Approximately 3 to 5 milligrams of the antigen, octylphenoxypoiyethylene oxide, are emulsified in Freund's Complete Adjuvant (FCA) and used to immunize a group of rabbits. After one week, an identical amount of antigen is emulsified with FCA, and the rabbit immunized again. Seven days following this booster injection, serum samples are taken from each rabbit, and the relative serum antibody titers determined by a solid phase enzyme linked immunosorbent assay (ELISA). Rabbits with highest titers are given a final regimen of antigen boosts over a period of three days, and used as spleen donors in fusions as described below. If titers are low after a second immunization, boosts will be repeated until an adequate titer is established.

Upon detection of antibody titer in immunized rabbit, immune splenocytes are harvested and a polyethylene glycol-mediated fusion performed using Balb/c-derived HGPRT (Hypoxanthine Guanine Phosphoribosyl Transferase) deficient SP2/0 plasmacytoma cell line. Fused cells are plated onto 96-well plates and the resultant hybridomas identified by selection in HAT medium. Supernatants from all viable hybridoma colines are tested for antibody production using an enzyme linked immunosorbent assay (ELISA). Cells from several positive wells are grown to produce cell stocks and cloned by the limiting dilution technique. Test tubes are then internally coated with the resulting monoclonal antibodies and the coated test tubes placed in a protective wrap.

The test tubes are placed in a box which also included a negative control, an enzyme conjugate of horseradish peroxide and the surfactant octylphenoxy-polyethylene oxide.

The substrate and chromogen were stabilized with buffer preparations of hydrogen peroxide and tetramethylbenzidine, respectively.

EXAMPLE III

Use of Immunoassay in Detection of Marker

To use the kit of Example II, the individual takes two test tubes out of their protective wrapping and places them in a foam insert provided in the kit. Into one test tube one places four drops of the negative control. Into the second test tube is placed four drops of the aqueous solution to be tested, i.e. the fourth rinsate of Example I. Four drops of the enzyme conjugate are added to both tubes and the tubes are shaken for five seconds and allowed to stand for five minutes. The liquid contents of tubes are then removed and the tubes rinsed four times with clean water. To each tube are added four drops of the substrate solution are added and then four drops of the chromogen solution with mixing. Within two or three minutes the color development should be sufficient to read a go/no-go decision. The development of a color equal to that of the negative indicates the absence of the marker. The lack of color indicates the presence of the marker and, therefore, the aqueous sample from the container indicates that the container still contains the product at levels above the established limits.

EXAMPLE IV

To a container containing a crop-protection chemical formulation is added 10% by weight of nonylphenoxypolyethylene oxide as a marker. The resulting composition comprises:

| | |
|---|---|
| Carbaryl | 44.0% |
| Water | 35.4% |
| surfactant | 6.0% |
| suspending aid | 3.0% |
| thickener | 0.5% |
| preservative | 0.1% |
| Marker | 10.0% |
| | 100.0% |

The crop chemical in this formulation is insoluble in both EPA approved water immiscible solvents and water itself. This water-based suspension of the compound carbaryl is then packaged as desired. The container is emptied and filled with 25% of its volume of clean water and shaken for at least 30 seconds. The rinsate is added to the application device and the procedure repeated three times. The container is discarded in a safe, approved manner. The application device now contains an intimate mixture of the suspended solids and the marker compound. The application mixture is sprayed onto apple trees and their fruit.

At a preselected time, sprayed apples are removed and rinsed with a given volume of water. The resulting aqueous rinsate is then tested for the presence of the marker by the immunoassay described in Example III.

EXAMPLE V

To a production vessel containing material ready for discharge to a waste treatment facility is added a metal salt of a dialkyl phenoxy(polyoxyethylene) phosphate ester. This product is selected as the marker because of its affinity to the oil phase and thus its movement will mimic that of the product which, for this example, is assumed to be relatively water insoluble.

The marker, dialkyl hydroxypoly(oxyethylene) phosphate ester and its corresponding magnesium salt, is added at a concentration suitable to provide detection after a given number of dilutions caused by the mixing in the downstream water.

Once the mixing in the vessel is complete, the contents can be discharged as per standard practice and water samples taken at the predetermined location. The water samples would then be analyzed by immunoassay using the immunoassay described in Example III.

EXAMPLE VI

To a production vessel containing an aqueous slurry of the biopesticide, Bacilluus thuringiensis, kurstaki, prior to its final packaging for commercial use, is added a blend of calcium-ammonium and sodium-calcium alginates as a marker. The final product has the following composition:

| | |
|---|---|
| *Bacillus thuringenius*, kurstaki | 2.5% |
| water, process inerts | 87.5% |
| mixed calcium-ammonium/sodium calcium alginate | 10.0% |
| | 100.0% |

The alginate marker is selected because it acts as a retardant for the evaporation of the water during application and as a binder and film former once the product hits the target. The use of this marker allows the analyst to determine how much product has hit the target. In an apple orchard collection trays are placed both underneath the apple trees (target) and between the trees (non-target) and the orchard is sprayed with the above composition. Trays from target areas and non-target areas are collected, emptied, water-rinsed and samples of a known volume of rinsate from each tested for the marker by the immunoassay described in Example III.

What is claimed:

1. A method of determining the amount of a contaminant substance remaining on a surface after the surface has be rinsed with water, said surface originally contacting a composition comprising a non-aqueous medium carrying a known concentration of said contaminant which forms an immisible, non-aqueous phase with water, comprising tagging said composition prior to said contacting and rinsing with a predetermined amount of a surface active agent;

contacting said surface with said tagged composition;

rinsing said surface with water to provide rinsate comprised of an aqueous phase and a non-aqueous phase containing said contaminant with said surface active agent associated with said contaminant and positioned between said two phases;

taking a sample of known volume of said rinsate; and determining the surface active agent in said rinsate sample without separating said aqueous phase, the determined amount of surface active agent relative to the predetermined concentration of said contaminant providing a measure of the amount of contaminant remaining on said surface.

2. A method according to claim 1 wherein the surface active agent is a non-ionic surface active agent.

3. A method according to claim 1 wherein the non-ionic surface active agent is alkaryl polyether alcohol.

4. A method according to claim 3 wherein the alkaryl polyether alcohol is selected from the group having the structure

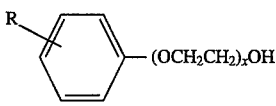

wherein R is a straight or branched alkyl of 8 to 9 carbon atoms and x is an integer of at least 1.

5. A method according to claim 4 wherein the amount of surface active agent is about 5 to 25% by weight of the composition.

6. A method according to claim 1 wherein the composition is an organic solvent-based solution.

7. A method according to claim 1 wherein the composition is a water-based suspension.

8. A method according to claim 1 wherein the composition is a water-based emulsion.

9. A method according to claim 1 wherein the composition is comprised of dry particles.

10. A method according to claim 1 wherein the contaminant is a crop protection chemical.

11. A method according to claim 1 wherein the contaminant is a hazardous material selected from the group consisting of paint, bleach, pool chemicals, fertilizers, disinfectants, drain opening chemicals, antifreeze chemicals and household cleaners.

12. A method according to claim 1 wherein the composition contains one or more surface active agents dissimilar to the surface active agent with which the composition is tagged.

13. A method of determining the amount of a contaminant substance remaining in a container after the container has been emptied and its interior rinsed with rinse water, said container originally containing a known contaminated volume of composition comprising a non-aqueous medium carrying a known concentration of said contaminant which forms an immisible, non-aqueous phase with water, comprising tagging said composition prior to said emptying and rinsing with a predetermined amount of surface active agent;

contacting said surface with said tagged composition;

rinsing said surface with water to provide a rinsate comprised of an aqueous phase and a non-aqueous phase of said contaminant with said surface active agent associated with said contaminant and positioned between said two phases;

taking a sample of said rinsate from said container after said emptying and rinsing, the volume of rinsate sample being known relative to said contaminated volume; and determining the amount of surface active agent in said rinsate sample without separating said aqueous phase, the determined amount of surface active agent relative to the predetermined concentration of said contaminant providing a measure of the amount of contaminant remaining in said container.

14. A method according to claim 13 wherein said rinsing comprises multiple rinsings.

15. A method according to claim 14 wherein each rinse is effected with a volume of water equal to 10–30% of the original volume.

16. A method according to claim 15 wherein a triple rinse is effected.

17. A method according to claim 13 wherein the interior of the empty container is pressure rinsed with water at a pressure of at least 40 psi for at least 30 seconds.

18. A method according to claim 13 wherein the container is a production vessel.

19. A method according to claim 1 wherein the determining of the amount of surface active agent is by immunoassay.

* * * * *